United States Patent
González Ballester et al.

(10) Patent No.: US 11,337,618 B2
(45) Date of Patent: May 24, 2022

(54) MEDICAL SYSTEM AND A DEVICE BASED ON MICROWAVE TECHNOLOGY FOR PREVENTION AND DIAGNOSIS OF DISEASES

(71) Applicants: UNIVERSITAT POMPEU FABRA, Barcelona (ES); UNIVERSITAT POLITÉCNICA DE CATALUNYA, Barcelona (ES); HOSPITAL CLÍNIC DE BARCELONA, Barcelona (ES); INSTITUTCIÓ CATALANA DE RECERCA I ESTUDIS AVANÇATS, Barcelona (ES)

(72) Inventors: Miguel Angel González Ballester, Barcelona (ES); Oscar Camara Rey, Barcelona (ES); Marta Guardiola Garcia, Barcelona (ES); Mario Ceresa, Barcelona (ES); Maria Gloria Fernández Esparrach, Barcelona (ES); Jordi Romeu Robert, Barcelona (ES)

( * ) Notice: Subject to any disclaimer, the term of this patent is extended or adjusted under 35 U.S.C. 154(b) by 598 days.

(21) Appl. No.: 16/071,130

(22) PCT Filed: Jan. 13, 2017

(86) PCT No.: PCT/IB2017/000011
§ 371 (c)(1),
(2) Date: Jul. 19, 2018

(87) PCT Pub. No.: WO2017/125807
PCT Pub. Date: Jul. 27, 2017

(65) Prior Publication Data
US 2021/0076973 A1   Mar. 18, 2021

(30) Foreign Application Priority Data
Jan. 20, 2016 (EP) .................................... 16152033

(51) Int. Cl.
*A61B 5/05* (2021.01)
*A61B 1/00* (2006.01)
(Continued)

(52) U.S. Cl.
CPC ........ *A61B 5/0507* (2013.01); *A61B 1/00131* (2013.01); *A61B 5/6847* (2013.01);
(Continued)

(58) Field of Classification Search
CPC ............................. A61B 5/0507; A61B 5/6852
See application file for complete search history.

(56) References Cited

U.S. PATENT DOCUMENTS 6,330,479 B1 * 12/2001 Stauffer ................... A61N 5/02
607/101
6,556,169 B1 * 4/2003 Fukuura .................. H01Q 1/38
343/700 MS
(Continued)

FOREIGN PATENT DOCUMENTS

| EP | 0048402 | 3/1982 |
| EP | 1121046 | 10/2004 |

(Continued)

OTHER PUBLICATIONS

International Search Report and written opinion dated Apr. 24, 2017 for PCT/IB2017/000011.
(Continued)

*Primary Examiner* — Colin T. Sakamoto
(74) *Attorney, Agent, or Firm* — Eugenio J. Torres-Oyola; Victor M. Rodriguez-Reyes; Rafael Rodriguez-Muriel

(57) ABSTRACT

The system comprising an internal unit (10) comprising two arrays of N transmitter and N receiver antennas (11R, 11T) for transmitting a microwave signal(s) to one or more body tissues of a patient and for detecting a scattered microwave signal(s) by said one or more body tissues; feeding and
(Continued)

multiplexing means (12) in connection with said N transmitter and N receiver antennas (11T, 11R) and with an external computing unit (20) configured to receive said scattered microwave signal(s) and convert it/them into an image, wherein the feeding and multiplexing means (12) provide, under the control of a controller (21) of the external computing unit (20), a continuous sequential selection of different pairs of transmitter and receiver antennas (11T, 11R) to perform the transmission of the microwave signal(s) and the detection of the scattered microwave signal(s).

8 Claims, 2 Drawing Sheets

(51) Int. Cl.
*H01Q 1/27* (2006.01)
*G01S 13/89* (2006.01)
*A61B 5/0507* (2021.01)
*A61B 5/00* (2006.01)
*H01Q 1/52* (2006.01)

(52) U.S. Cl.
CPC ............ *A61B 5/6852* (2013.01); *G01S 13/89* (2013.01); *H01Q 1/273* (2013.01); *A61B 2562/043* (2013.01); *H01Q 1/523* (2013.01); *H01Q 1/525* (2013.01)

(56) References Cited

U.S. PATENT DOCUMENTS

| | | | |
|---|---|---|---|
| 2003/0036713 A1* | 2/2003 | Bouton | A61B 5/05 600/587 |
| 2009/0292242 A1* | 11/2009 | Konishi | A61B 5/02007 604/103.05 |
| 2012/0212380 A1* | 8/2012 | Theobold | A61B 5/08 343/720 |
| 2012/0330151 A1* | 12/2012 | Weinstein | A61N 1/36578 600/427 |
| 2013/0345541 A1 | 12/2013 | Nau, Jr. | |
| 2016/0199131 A1* | 7/2016 | Allison | A61B 18/18 606/13 |
| 2017/0172655 A1* | 6/2017 | Allison | A61B 5/0507 |

FOREIGN PATENT DOCUMENTS

| | | |
|---|---|---|
| WO | 2010049523 | 5/2010 |
| WO | 2013005134 | 1/2013 |
| WO | 2014149183 | 9/2014 |

OTHER PUBLICATIONS

International Search Report and written opinion dated Jul. 29, 2016 for EP priority application No. 16152033.3.

* cited by examiner

MEDICAL SYSTEM AND A DEVICE BASED ON MICROWAVE TECHNOLOGY FOR PREVENTION AND DIAGNOSIS OF DISEASES

RELATED APPLICATIONS

This application is the US national phase application of international application number PCT/IB2017/000011, filed 13 Jan. 2017, which designates the US and claims priority to European application EP 16152033.3 filed 20 Jan. 2016, the contents of each of which are hereby incorporated by reference as if set forth in their entireties.

TECHNICAL FIELD

The present invention is directed, in general, to the field of medical systems for treating diseases. In particular, the invention relates to a medical system, and to a device, based on microwave technology for prevention and diagnosis of diseases such as cancers, for example colorectal cancers, among other pathologies.

BACKGROUND OF THE INVENTION

Most cancers arise from precursor lesions, for example colorectal cancers arise from adenomatous polyps according to the adenoma-carcinoma sequence. In recent years there have been many improvements in image quality provided by currently available endoscopes, HD endoscopes, complementary functions such as electronic chromoendoscopy NBI (Narrow Band Imaging) and image magnification. However, the use of these resources makes scanning more laborious and therefore longer and requires specific training for the endoscopist. Because of these limitations of traditional endoscopy, more innovative alternatives such as computer vision techniques appeared. However, these techniques are based on the information provided by the optical camera of the endoscope and rely on the image since most of the studies are based on the description of morphological characteristics such as shape or texture to determine the existence of a polyp.

Another non-invasive emerging technique is microwave imaging. This technique does not rely on optical images. Microwave signals penetrate light opaque materials and operate a new contrast mechanism based on the dielectric properties of the tissues. Each tissue has its own dielectric properties that vary according to their conditions (hypoxia, ischemia, neoplasm, etc.). Microwave imaging systems can sense the dielectric properties of the human body and obtain an image of the tissue distribution and their pathological conditions without requiring direct contact. Microwaves are applied in the field of medicine since the 80s for both treatment (hyperthermia and ablation) and diagnosis. Breast cancer and cerebral hemorrhage detection are the most well-known applications. The main advantages of microwaves are safety (non-ionizing and low power radiation) and low cost, making microwaves a powerful technique for monitoring and prevention.

Microwave imaging systems can provide information in many endoscopic or catheter-based mapping applications as in a colonoscopy or in the heart electro-anatomic mapping.

US-A1-2013345541 discloses an electrosurgical system for imaging and interrogating tissue. The electrosurgical system includes an energy source configured to generate a first energy and an electrosurgical instrument comprising a transmission line coupled to the energy source and configured to emit the first energy. A mirror reflects the first energy towards a target tissue that emits a second energy. An ultrasonic transducer receives the second energy from the target tissue and converts the second energy into an electrical signal. A controller receives the electrical signal and converts the electrical signal into an image. Contrary to the present invention, the electrosurgical system of this patent application does not include arrays of transmitter and receiver antennas which are working sequentially for transmitting a first energy and for detecting a second energy signals.

EP-B1-1121046 discloses a method of treatment using implantable devices that comprises implanting into the body of a human or a non-human animal a rectenna capable of receiving electromagnetic radiation in the microwave frequency range and of generating and/or storing electrical energy therefrom; and an electrically operated therapeutic device arranged to receive electrical energy from said rectenna; and directing electromagnetic radiation in the microwave frequency range from a source external to the body being treated towards the position of the implanted rectenna so as to generate electrical energy to actuate said therapeutic device. Unlike the present invention, this patent does not execute a sequential selection of pairs of transmitting and receiving antennas to transmit energy signals to the tissue and to detect the energy signal scattered by said tissue.

WO-A2-2014149183 discloses a system including a microwave antenna probe for transmitting and receiving electromagnetic signals to detect one or more markers that are implanted within or around the target tissue region. During use, the marker(s) are implanted into a target tissue region, and the microwave antenna probe is placed against the patient's skin to transmit a signal to the marker(s) and to receive the reflected signal from the marker(s) in order to determine the location of the marker(s). Unlike the present invention, in this patent application the means transmitting the microwave signals does not comprise two arrays of N transmitter and N receiver antennas, nor comprises an internal unit having feeding and multiplexing means in connection with said N transmitter and N receiver antennas, for providing, under the control of a controller a continuous sequential selection of different pairs of transmitter and receiver antennas to perform the transmission of the microwave signal and the detection of the scattered microwave signal.

WO-A2-2013005134 discloses methods and systems to image an object of interest using one or more probes, particularly by delivering electromagnetic energy (e.g., microwave energy) using a transmitting antenna to the object while activating a probe to interact with the scattered field and sampling the resulting scattered field using one or more receiving antennas. The sampled electromagnetic energy may then be used to reconstruct an image of the object. In this patent application, various antenna configurations (e.g., changing over time) may be used to deliver the electromagnetic energy.

It is desirable to provide, therefore, new medical systems and devices based on microwave technology for prevention and diagnosis of diseases such as cancers (e.g. colorectal cancers, among other types of cancers) with greater precision and using new methods not based on vision.

DESCRIPTION OF THE INVENTION

To that end the present invention proposes, according to one aspect, a medical system based on microwave technology for prevention and diagnosis of diseases, said system comprising as commonly in the field, an internal unit which, in use, is introduced within a body passage of a patient (e.g. the colon, the stomach, the esophagus, the trachea, etc.), including means for transmitting a first energy signal to one or more body tissues and for detecting a second energy signal scattered by said one or more tissues; and an external computing unit (e.g. a personal computer (PC), a Smartphone, etc.) which, in use, is located outside the body of the patient and connected with said internal unit to receive said second energy signal detected by said internal unit and to convert said received second energy signal into an image.

Contrary to the known proposals, in the proposed medical system the means for transmitting a first energy signal and for detecting a second energy signal of the internal unit comprises two arrays of N transmitter and N receiver antennas, said first and second energy signals comprising microwave signals (from about 3 to about 10 GHz).

In addition, the internal unit also includes feeding and multiplexing means in connection with said N transmitter and N receiver antennas and with said external computing unit, for providing, under the control of a controller located in said external computing unit, a continuous sequential selection of different pairs of transmitter and receiver antennas to perform the transmission of the microwave signal and the detection of the scattered microwave signal.

In accordance with an embodiment, the N transmitter and N receiver antennas and the feeding and multiplexing means are arranged on a same electronic substrate having two faces, the N transmitter (preferably at least four) and N receiver (preferably at least four) antennas being positioned on one of said two faces and the feeding and multiplexing means being positioned on the other face.

Moreover, the internal unit also includes a protective shell for protection of the two arrays of N transmitter and N receiver antennas and the feeding and multiplexing means. According to the invention, the protective shell is made of biocompatible materials and is designed to achieve a good tightness and resistance to disinfectants used in high-grade disinfection processes.

Preferably, the internal unit is of a cylindrical shape to be coupled to an endoscope tube or catheter tube.

Preferably, each of said N transmitter antennas and each of said N receiver antennas is connected to a radiofrequency switch by means of radiofrequency (RF) transmission lines. Besides, the N transmitter and N receiver antennas are positioned at a distance of at least half a wavelength.

The external computing unit may be connected to the feeding and multiplexing means either via a wireless connection or via a wired connection including an optical fiber connection or a coaxial cable, among others. A battery can be also used to feed the antennas.

In accordance with an embodiment, the controller of the external computing unit is configured to select at each continuous sequential selection a single pair of transmitter and receiver antennas.

Other embodiments of the invention that are disclosed herein include also a device based on microwave technology for prevention and diagnosis of diseases, said device being configured to be coupled to an endoscope or catheter tube and comprising means for or to be controlled by an external computing device (e.g. a PC, a Smartphone, a notebook, a tablet, etc.).

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF PREFERRED EMBODIMENTS

Figure 1:
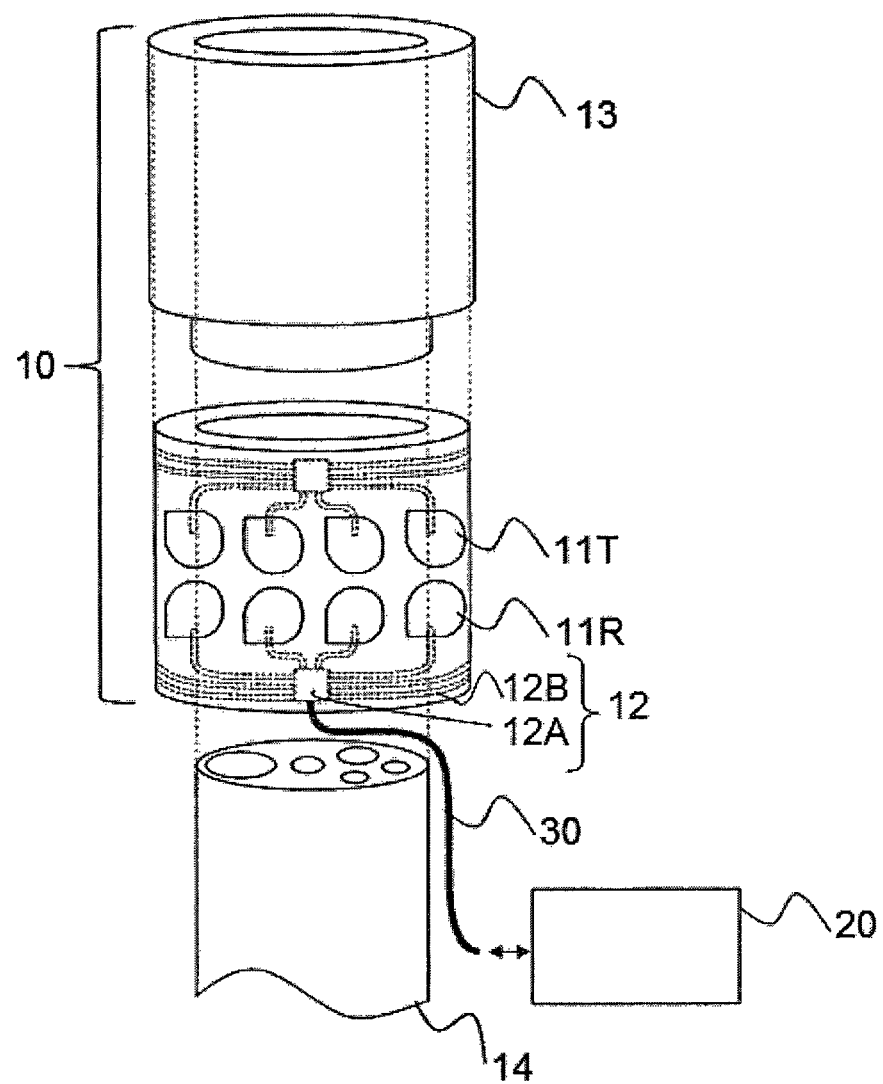
FIG. 1 illustrates in a simplified way a medical system based on microwave technology for prevention and diagnosis of diseases according to an embodiment of the present invention.

FIG. 1 shows an embodiment of the proposed architecture of the medical system of the invention for prevention and diagnosis of diseases such as cancers, among any other pathologies/diseases.

Figure 2:
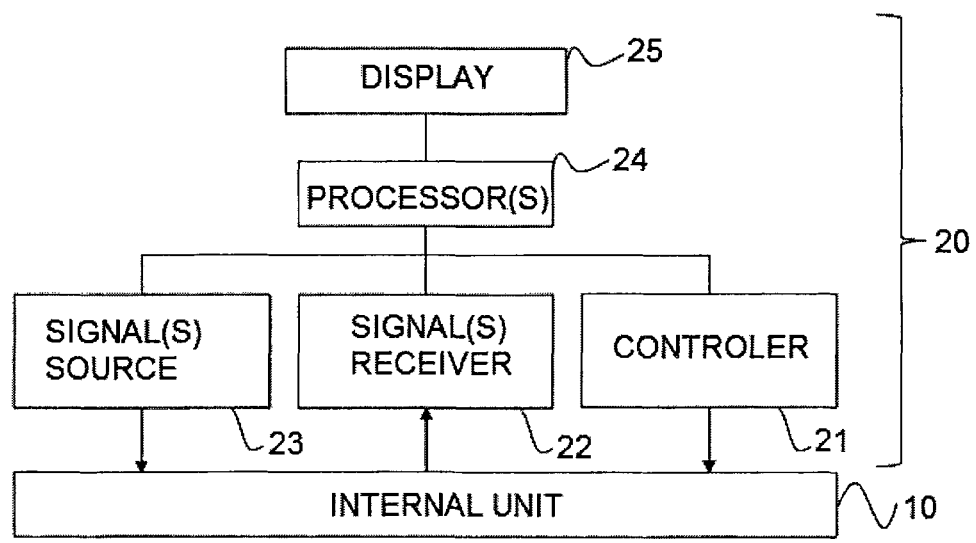
FIG. 2 is a schematic block diagram illustrating some of the units/modules provided by the proposed medical system according to the teachings of present invention.

According to said embodiment, present invention comprises an internal unit 10, preferably of a cylindrical shape (not limitative as other geometric shapes are also possible) that can be coupled to an endoscope or catheter tube 14, to be introduced, in use, within a body passage (or internal area) of a patient (not illustrated) such as the colon, the stomach, the esophagus, the trachea, etc., and an external computing unit 20 such as a PC operatively connected to the internal unit 10 for signal generation 23, signal receiving 22, storage, processing 24 and display 25 (see FIG. 2).

The internal unit 10 according to this embodiment comprises one linear array of four transmitter antennas 11T configured and arranged for transmitting a microwave signal (or signals) to one or more body tissues of the patient, a linear array of four receiver antennas 11R configured and arranged for detecting a microwave signal (or signals) scattered by the one or more body tissues, feeding and multiplexing means 12 in connection with the four transmitter and receiver antennas 11T, 11R and with the external computing unit 20, and a protective shell 13 enclosing the antennas 11T, 11R and the feeding and multiplexing means 12.

The three parts of the internal unit 10 (i.e. the two linear arrays of transmitter and receiver antennas 11T, 11R, the feeding and multiplexing means 12 and the protective shell 13) are specifically designed taking into account important constraints of size and reprocessing of medical devices.

According to said embodiment, the two linear arrays of transmitter and receiver antennas 11T, 11R are printed on a top layer of an electronic substrate and the feeding and multiplexing means 12 on the bottom layer of said electronic substrate. The receiving array 11R is set below the transmitting array 11T, has the same characteristics and is separated at a distance of at least half a wavelength to reduce the coupling between the arrays of antennas. The transmitter and receiver antennas 11T, 11R are preferably compact printed slots.

The feeding and multiplexing means 12 are composed by a Radiofrequency (RF) switch 12A and N RF transmission lines 12B for each array of transmitter 11T and receiver 11R antennas.

The outer protective shell 13 is designed to achieve good sealing and resistance to disinfectants used in the process of high-level disinfection.

It has to be noted that even the embodiment of FIG. 1 comprises only four transmitter 11T and four receiver antennas 11R present invention is not limited to this configuration, as other amount of pairs of antennas are also possible, for instance a configuration 2×2 (two transmitter and two receiver antennas), 3×3 (three transmitter and three receiver antennas), 5×5 (five transmitter and five receiver antennas), 8×8 (eight transmitter and eight receiver antennas), among others. Equally, even though in the embodiment of FIG. 1 the array is a linear array, other array configuration may be also possible without departing from the scope of protection of present invention.

To form a cross-sectional image of the body tissue of the patient being irradiated, the body tissue has to be irradiated from all the directions (360°). To do so, the transmitter and receiver antennas 11T, 11R are controlled by a controller 21 (see FIG. 2), such as a micro-controller, of the external computing device 20, through the feeding and multiplexing means 12, i.e. through the RF switches 12A and RF transmission lines 12B, to perform the emission and detection of microwave signals via a continuous selection. The controller 21 continuously selects pairs of antennas (transmitter-receiver) for performing the microwave signal emission and the microwave signal detection. Preferably, at each continuous selection a single pair of transmitter-receiver antennas 11T, 11R is selected, repeating the process until enough signals are collected to form the image of the irradiated body tissue.

The generation of the microwave signal and the selection of the transmitting and receiving antennas 11T, 11R is performed automatically and synchronized with the transmission and acquisition by the external computing device 20.

According to this embodiment, the microwave signals are generated by the external computing device 20 and delivered to the internal unit 10 by means of a wired connection including a thin coaxial cable 30 along the endoscope or catheter tube 14 as illustrated in FIG. 1. Alternatively, the wired connection instead of said coaxial cable 30 may include a fiber optical cable.

The scattered signals received by the external computing unit 20 from the receiver antennas 11R are processed with microwave image reconstruction algorithms including frequency and time-domain dielectric property estimation methods, radar methods or tomographic imaging. Microwave information will be combined with the existing endoscopic visualization tools providing all the available data with the same interface, which can include video, microwave imaging, endoscope tracking, and previous CT imaging.

According to an alternative embodiment, in this case not illustrated, the microwave signals generated by the external computing device 20 are delivered to the internal unit 10 via wireless technology (i.e. no cables are present between the external computing device 20 and the internal unit 10). At the device, then the transmitting signal is multiplexed and delivered to the transmitting antennas 11T through the feeding and multiplexing means 12.

The invention further refers to a device 10, preferably of a cylindrical shape, which in use, is introduced within a body passage of a patient (e.g. the colon) and configured and adapted to work with microwave technology (approximately 3 to 10 GHz) for prevention and diagnosis of diseases. The device 10, comprises two arrays of N transmitter and N receiver antennas 11T, 11R which, in use, are configured to emit, by the transmitter antennas 11R, a first microwave signal to one or more body tissues and to detect, by the receiver antennas 11R, a second microwave signal scattered by said one or more body tissues; and feeding and multiplexing means 12 in connection with said N transmitter and N receiver antennas 11T, 11R and with an external computing unit 20 such as a PC.

The scope of the present invention is defined in the following set of claims.

The invention claimed is:

1. A medical system based on microwave technology for prevention and diagnosis of diseases, said system comprising:
an internal unit which, in use, is introduced within a body passage of a patient, said internal unit including:
a first array of N transmitter antennas configured to transmit a first energy signal to one or more body tissues and a second array of N receiver antennas configured to detect a second energy signal scattered by the one or more body tissues, said first and second energy signals comprising microwave signals; and
feeding and multiplexing elements in connection with the N transmitter and N receiver antennas and with an external computing unit,
wherein the N transmitter and N receiver antennas and the feeding and multiplexing elements are arranged on a same electronic substrate having two faces, the N transmitter and N receiver antennas being positioned on one of said two faces and the feeding and multiplexing elements being positioned on the other face; and
said external computing unit which, in use, is located outside the body of the patient and connected with said internal unit to receive said second energy signal detected by said internal unit and to convert said received second energy signal into an image,
wherein the feeding and multiplexing elements are configured to provide, under the control of a controller that the external computing unit comprises, a continuous sequential selection of different pairs of transmitter and receiver antennas to perform the transmission of the microwave signal and the detection of the scattered microwave signal.

2. The system of claim 1, wherein the feeding and multiplexing elements comprise a Radiofrequency switch and N Radiofrequency lines for each of said first and second arrays, such that each of the N transmitter antennas is connected to a first Radiofrequency switch using a first set of N Radiofrequency lines and each of the N receiver antennas is connected to a second Radiofrequency switch using a second set of N Radiofrequency lines.

3. The system of claim 1, wherein the first array comprises at least two transmitter antennas and wherein the second array comprises at least two receiver antennas.

4. The system of claim 1, wherein the controller of the external computing unit is configured to select at each continuous sequential selection a single pair of transmitter and receiver antennas.

5. The system of claim 1, further comprising a protective shell configured to protect the first and second arrays and the feeding and multiplexing elements.

6. The system of claim 1, wherein the external computing unit is connected through a wired connection to said feeding and multiplexing elements.

7. The system of claim 1, wherein the external computing unit is connected through a wireless connection to said feeding and multiplexing elements.

8. The system of claim 1, wherein the internal unit is of a cylindrical shape to be coupled to an endoscope tube.

* * * * *